(12) United States Patent
Jaggi

(10) Patent No.: US 8,409,851 B2
(45) Date of Patent: Apr. 2, 2013

(54) BIOACTIVE CARBON DIOXIDE FILTER APPARATUS AND METHOD THEREFOR

(76) Inventor: Param Jaggi, Plano, TX (US)

( * ) Notice: Subject to any disclaimer, the term of this patent is extended or adjusted under 35 U.S.C. 154(b) by 696 days.

(21) Appl. No.: 12/655,233

(22) Filed: Dec. 23, 2009

(65) Prior Publication Data

US 2010/0190241 A1 Jul. 29, 2010

Related U.S. Application Data

(60) Provisional application No. 61/203,564, filed on Dec. 23, 2008.

(51) Int. Cl.
| | |
|---|---|
| *A01G 7/00* | (2006.01) |
| *A01H 13/00* | (2006.01) |
| *C12M 1/36* | (2006.01) |
| *C12M 1/38* | (2006.01) |
| *C12M 1/12* | (2006.01) |
| *C12M 1/09* | (2006.01) |
| *C12M 1/00* | (2006.01) |
| *C12M 3/00* | (2006.01) |
| *C12M 1/24* | (2006.01) |

(52) U.S. Cl. ......... 435/292.1; 47/1.4; 47/17; 435/257.1; 435/286.6; 435/286.7; 435/296.1; 435/304.1

(58) Field of Classification Search ............... 435/292.1, 435/257.1, 286.6, 286.7, 296.1, 304.1; 47/1.4, 47/17

See application file for complete search history.

(56) References Cited

U.S. PATENT DOCUMENTS

2005/0239182 A1* 10/2005 Berzin ........................ 435/166
2009/0305389 A1* 12/2009 Willson et al. ............. 435/257.1

\* cited by examiner

*Primary Examiner* — Nathan Bowers
*Assistant Examiner* — Lydia Edwards
(74) *Attorney, Agent, or Firm* — Schultz & Associates, P.C.

(57) ABSTRACT

A bioactive filter is provided which comprises a transparent canister having gas permeable membranes as entry and exit ports. A source of carbon dioxide in gaseous form is allowed to enter the entry membrane and pass through a solution contained in the canister which supports a live colony of algae. The algae carries out photosynthesis thereby altering the carbon dioxide to oxygen and sugar. The oxygen is released through the exit port.

11 Claims, 6 Drawing Sheets

BIOACTIVE CARBON DIOXIDE FILTER APPARATUS AND METHOD THEREFOR

CROSS-REFERENCE TO RELATED APPLICATIONS

This application claims priority to U.S. Provisional Application No. 61/203,564, entitled "Creating An Anti-Pollutant Device Based Upon Algae and Enzymes," filed Dec. 23, 2008.

TECHNICAL FIELD OF THE INVENTION

The present invention relates to emission control devices. More specifically, the invention relates to devices that reduce the level of gaseous carbon exhaust products resulting from combustion engines. Gaseous carbon dioxide is converted into oxygen through a photosynthesis process carried out by algae encapsulated within a canister used as a filter in the exhaust stream.

BACKGROUND OF THE INVENTION

The world faces various problems of global warming and pollution that has brought disparity to societies across the world. Global warming has caused damage in all parts of our society from the fluctuation of weather to affecting the lifestyles of common animals. Humans have created an environment that has become accustomed to more precarious living conditions through the decades of increase in technology. These technologies that harm our atmosphere include factories, oil stations, and trains. One of the most dangerous of these technologies to our environment has shown to be the automobile. With an estimated 78% of the world's global pollution and a significant contributor to greenhouse gasses, the automobile has become a daily liability that is used by over 70 million people in the United States. With 70 million people driving at least 1 automobile daily, the world seems to come to its disparity when looking to global pollution and the effects on our natural world. These rising pollutant rates can be tackled through three main aspects of our environmental control: a) cleaner fuel; b) cleaning the physical atmosphere and ozone layer; or c) reducing the carbon dioxide in its first stage of pollution through a primary source such as automotive exhaust.

Estimates have been made that Earth's atmosphere has accumulated over 5,000 tons of carbon dioxide. These estimates can be seen as an accumulation of all greenhouse contributors. And because vehicles contribute up to 78% of these 5,000 tons of carbon dioxide, controlling vehicle emissions is of primary concern.

Vehicle pollution is primarily caused by the exhaust emissions from internal combustion engines. Emissions, including gaseous carbon dioxide, carbon monoxide and diatomic nitrogen are sent through the exhaust system where they are simply released into the atmosphere. The amount of carbon dioxide in the exhaust is only reduced by 15% by current emissions control components such as catalytic converters. Thus 85% of the original carbon dioxide escapes into the atmosphere. The exhaust system itself serves as a passage way to the outside world rather than as a benefactor to the environment.

Combustion or burning is the sequence of exothermic chemical reactions between a fuel and an oxidant accompanied by the production of heat and conversion of chemical species. The release of heat can result in the production of light in the form of either glow or a flame. Most fuels of interest are organic compounds (especially hydrocarbon) in the gas, liquid or solid phase.

In a complete combustion reaction, a compound reacts with an oxidizing element, such as oxygen or fluorine, and the products are compounds of each element in the fuel with the oxidizing element. For example:

$$CH_4 + 2O_2 \rightarrow CO_2 + 2H_2O$$

$$CH_2S + 6F_2 \rightarrow CF_4 + 2HF + SF_6$$

A simpler example can be seen in the combustion of hydrogen and oxygen, which is a commonly used reaction in rocket engines:

$$2H_2 + O_2 \rightarrow 2H_2O(g) + \text{heat}$$

The result is water vapor.

In the large majority of industrial applications of combustion and in fires, air is the source of oxygen ($O_2$). In air, each kg (lbm) of oxygen is mixed with approximately 3.76 kg (lbm) of nitrogen. The resultant flue gas from the combustion will contain nitrogen:

$$CH_4 + 2O_2 + 7.52N_2 \rightarrow CO_2 + 2H_2O + 7.52N_2 + \text{heat}$$

In complete combustion, the reactant will burn in oxygen, producing a limited number of products. When a hydrocarbon burns in oxygen, the reaction will only yield carbon dioxide and water. When a hydrocarbon or any fuel burns in air, the combustion products will also include nitrogen. When elements such as carbon, nitrogen, sulfur and iron are burned, they will yield the most common oxides. Carbon will yield carbon dioxide. Nitrogen will yield nitrogen dioxide. Sulfur will yield sulfur dioxide. Iron will yield iron(III) oxide. It should be noted that complete combustion is almost impossible to achieve. In reality, as actual combustion reactions come to equilibrium, a wide variety of major and minor species will be present. For example, the combustion of methane in air will yield, in addition to the major products of carbon dioxide and water, the minor side reaction products carbon monoxide and nitrogen oxides.

Incomplete combustion occurs when there is not enough oxygen to allow the fuel (usually a hydrocarbon) to react completely with the oxygen to produce carbon dioxide and water, also when the combustion is quenched by a heat sink such as a solid surface or flame trap. When a hydrocarbon burns in air, the reaction will yield carbon dioxide, water, carbon monoxide, pure carbon (soot or ash) and various other compounds such as nitrogen oxides.

Automobiles produce many different pollutants. The principal pollutants of concern are those that have been demonstrated to have significant effects on human, animal, plant, environmental health and welfare. Such pollutants include:

Hydrocarbons: this class is made up of unburned or partially burned fuel, and is a major contributor to urban smog, as well as being toxic. They can cause liver damage and even cancer. The regulations regarding hydrocarbons vary according to the engine regulated, as well as the jurisdiction. In some cases, "non-methane hydrocarbons" are regulated, while in other cases, "total hydrocarbons" are regulated. Technology for one application (to meet a non-methane hydrocarbon standard) may not be suitable for use in an application that has to meet a total hydrocarbon standard. Methane is not toxic, but is more difficult to break down in a catalytic converter, so in effect a "non-methane hydrocarbon" standard can be considered to be looser. Since methane is a greenhouse gas, interest is rising in how to eliminate emissions of it.

Carbon monoxide (CO): a product of incomplete combustion, carbon monoxide reduces the blood's ability to carry oxygen and is dangerous to people with heart disease.

Nitrogen oxides ($NO_x$): These are generated when nitrogen in the air reacts with oxygen at a high temperature and pressure inside the engine. $NO_x$ is a precursor to smog and acid rain. $NO_x$ is a mixture of NO and $NO_2$. $NO_2$ destroys resistance to respiratory infection. For dogs most of the nitrogen dioxide is removed in the nasal cavity. Large vehicles such as delivery trucks emit hot exhaust, containing life threatening quantities of $NO_2$. The quantities are great enough that individuals with known respitory weaknesses are at risk.

Carbon dioxide ($CO_2$): $CO_2$ is not a pollutant per se, but is a greenhouse gas and so plays a role in global warming. The only way to reduce $CO_2$ emission is to burn less fuel.

Particulates: soot or smoke made up of particles in the micrometer size range: Particulate matter causes respiratory health effects in humans and animals.

Sulphur oxides ($SO_x$): A general term for oxides of sulphur, which are emitted from motor vehicles burning fuel containing a high concentration of sulphur.

Applicant has realized that the photosynthesis reaction and cellular respiration carried out by several specific algae species are capable of recovering a significant portion of gaseous carbon dioxide present in and resulting from incomplete combustion of fossil fuels.

Photosynthesis splits water to liberate $O_2$ and transforms $CO_2$ into sugar. Photosynthetic organisms are photoautotrophs, which means that they are able to synthesize food directly from carbon dioxide using energy from light. However, not all organisms that use light as a source of energy carry out photosynthesis, since photoheterotrophs use organic compounds, rather than carbon dioxide, as a source of carbon. In plants, algae and cyanobacteria, photosynthesis releases oxygen. This is called oxygenic photosynthesis. Although there are some differences between oxygenic photosynthesis in plants, algae and cyanobacteria, the overall process is quite similar in these organisms. However, there are some types of bacteria that carry out anoxygenic photosynthesis, which consumes carbon dioxide but does not release oxygen.

Carbon dioxide is converted into sugars in a process called carbon fixation. Carbon fixation is a redox reaction, so photosynthesis needs to supply both a source of energy to drive this process, and also the electrons needed to convert carbon dioxide into a carbohydrate, which is a reduction reaction. In general, photosynthesis is the opposite of cellular respiration, where glucose and other compounds are oxidized to produce carbon dioxide, water, and release chemical energy. However, the two processes take place through a different sequence of chemical reactions and in different cellular compartments.

The general equation for photosynthesis is therefore:

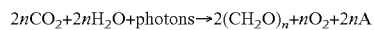

Carbon dioxide+electron donor+light energy→carbohydrate+oxygen+oxidized electron donor Since water is used as the electron donor in oxygenic photosynthesis, the equation for this process is:

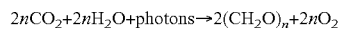

carbon dioxide+water+light energy→carbohydrate+oxygen

Other processes substitute other compounds (such as arsentite) for water in the electron-supply role; the microbes use sunlight to oxidize arsenite to arsenate The equation for this reaction is:

carbon dioxide+arsenite+light energy→arsenate+carbon monoxide(used to build other compounds in subsequent reactions)

Photosynthesis occurs in two stages. In the first stage, light-dependent reactions or light reactions capture the energy of light and use it to make the energy-storage molecules ATP and NADPH. During the second stage, the light-independent reactions use these products to capture and reduce carbon dioxide. Most organisms that utilize photosynthesis to produce oxygen use visible light to do so, although at least three use infrared radiation.

*Chlorella* is a very common algae type that has demonstrated useful qualities in the invention. *Chlorella* is a genus of single-celled green algae, belonging to the phylum Chlorophyta. It is spherical in shape, about 2 to 10 μm in diameter, and is without flagella. *Chlorella* contains the green photosynthetic pigments chlorophyll-a and -b in its chloroplast. Through photosynthesis it multiplies rapidly requiring only carbon dioxide, water, sunlight, and a small amount of minerals to reproduce. Its photosynthetic efficiency can, in theory, reach 8%, comparable with other highly efficient crops such as sugar cane. Further, its rigid cell walls are unusually resistant to deterioration from heat and cold.

SUMMARY OF THE INVENTION

A primary purpose of the embodiments is to decrease the levels of carbon dioxide within the exhaust system of an internal combustion engine and other sources of carbon dioxide.

The dimensions and construction materials of the device are important. In one embodiment, the device comprises a replaceable canister or cartridge. In a preferred embodiment, the canister attaches to the exhaust manifold of an internal combustion engine by means of an adjustable quick connector system. In use one filter may be exchanged for another, while safely retaining the liquid inside both the old and new cartridges.

Another aspect of a preferred embodiment of the invention is the use of titanium and alloys of titanium in construction of the canister cartridge and filter elements. The heat transfer characteristics of titanium and titanium alloys assist in conducting heat away from the sensitive biological elements contained. Furthermore, mechanical heat sinks constructed of titanium and titanium alloy on the interior and exterior of the canister increase both convective and radioactive heat transfer properties in a favorable way.

Another aspect of the device is the unidirectional flow of the carbon dioxide gas through the device. Tubes and surrounding filter parts are designed to create an optimal condition for the algae. The device prevents return exhaust flow into the passenger compartment or engine components. The device prevents sudden malfunction of the engine and the surrounding parts. The device allows vastly reduced flow restriction allowing more efficient and stable bio reaction and carbon dioxide decontamination.

One embodiment provides for controlled exiting of the oxygen once the conversion of carbon dioxide has taken place. In this embodiment, there is no restriction of the flow of exhaust gases. However, to increase the flow of oxygen, the exit port of the device consists of a small membrane that has fine holes that allow a release of oxygen while retaining the liquid within the filter.

Another embodiment of the invention comprises a canister containing a solution of live *Chlorella* algae and bounded by entry and exit membranes capable of gaseous transmission but restricting fluid transmission.

An important aspect of the device is to preserve algae viability. The algae must be maintained at a non-lethal temperature despite the heat from the exhaust gases and surrounding components. To cool the algae when the device is in use, mechanical heat sinks both internal and external to the canister are provided. To keep the algae warm, a coat of insulation surrounds the device to sustain the algae in extreme temperatures.

Another aspect of the device is the configuration of the algae within the device. In one embodiment, algae must be kept at or near the center of the device in order to maximize the protection of the insulation. Additionally, when placing the initial colony of algae within the device, sufficient space must be left within the device to account for algae growth. Where environmental conditions permit, algae may be attached to the inner walls of the algae filter, as well as any structures within the filter. The structures are designed to center the algae within the device thereby allowing it free access to nutrients and light energy.

BRIEF DESCRIPTION OF THE DRAWINGS

Reference will be made to the accompanying drawings, which are not necessarily drawn to scale.

DETAILED DESCRIPTION OF THE INVENTION

This invention may be embodied in many different forms and should not be construed as limited to the embodiments described. The embodiments are provided by way of example.

The first aspect of the design, which is imperative to the conversion of the carbon dioxide into oxygen, is the algae and fluid within the canister. The algae are grown in a glass container which is 51×24.5×29 cm and is grown for approximately 4-6 weeks for optimal production of oxygen. The algae are kept in optimal conditions to increase reproduction within the colonies. The procedure for growing the algae will be described later.

In order to create a living colony of algae, a tank is filled with water and placed outside in the sunlight. It is preferable for the tanks to be clear on all sides in order to allow the maximum amount of sunlight into the tank and promote photosynthesis within the algae. It may be necessary to condition the water for algae growth depending on the source of the water. For example, the ph of the water may be too high to support optimal growth of the algae.

In a preferred embodiment of the tank colony, there are multiple clear-walled tanks each approximately 51×25×29 cm. Approximately 40 liters of water is added to each tank and allowed to settle for 24 hours. At this point, the water is in condition to remove any offending minerals, salt or to balance the ph. After conditioning, sand or dirt is added to the tank and allowed to settle. A starter colony of algae is then added. In a preferred tank colony, the algae are *Chlorella* algae. The tanks are then placed in the sunlight. The tanks should remain undisturbed for a week or until a sufficiently large colony of algae forms within.

In the preferred embodiment the following steps were performed to obtain suitable *Chlorella* algae:
1. Pour 10 gallons of the water into one glass tank with dimensions 51×24.5×20 cm;
2. Allow the water to settle for at least 24 hours;
3. Repeat steps 1-3 for an additional 8 tanks;
4. Add sand/dirt to the bottom of each tank, and after the sand/dirt settles, pour 2 vials of the algae, *Chlorella*, into a single tank;
5. Place the tank of algae and water into direct sunlight in order for the algae to grow;
6. Wait a week for the algae to fully develop; and
7. Separate the algae into eight equal amounts, and place each amount into the eight tanks not yet exposed to algae.

Also in a preferred embodiment, the liquid contained is provided with a dispersion of iron sulfate within liquid water to serve as nutrients for algae colonies. Other nutrients, provided in this and other embodiments more suitable for different strains of algae.

Figure 1:
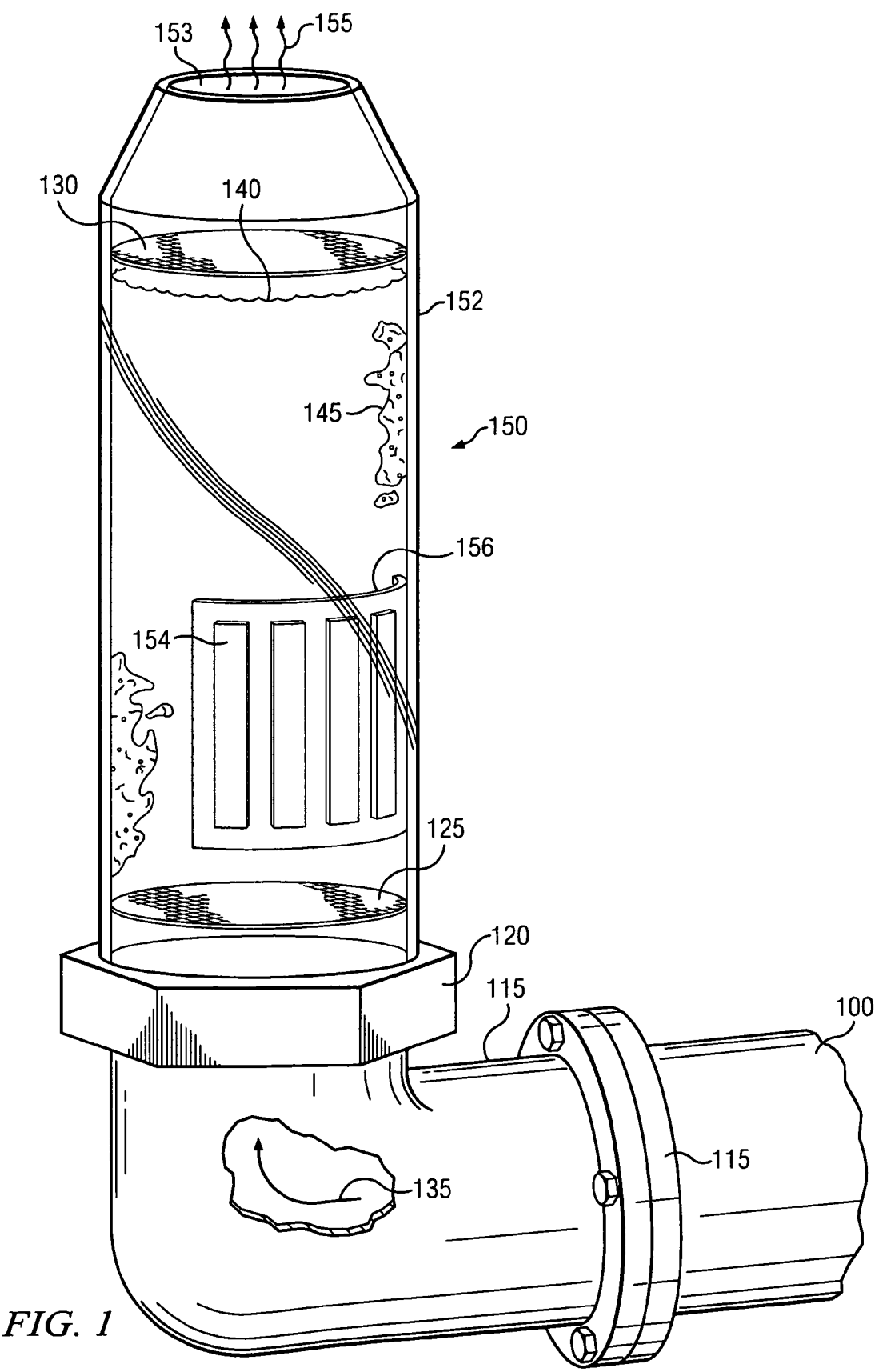
FIG. 1 shows an embodiment lacking any barriers between the gases and liquid.

FIG. 1 shows a first embodiment of filter 150. Connecting pipe 115 is attached to exhaust pipe 100 by exhaust connector 110 of an internal combustion engine (not shown) and removable connector 120. Removable connector 120 connects to filter 150 and provides a ducted passage between the connecting pipe and the filter. The filter includes of transparent body 152. In the preferred embodiment transparent canister 251 is formed of Lexan (plexiglass). Other biologically inert plastics will suffice. Algae 145 is cultured on the interior of transparent body 152. Entry membrane 125 and exit membrane 130 are attached at opposite ends of transparent body 152, containing liquid 140. Entry membrane 125 and exit membrane 130 are semi-permeable membranes that allow gases to enter and exit while preventing the passage of fluids. The liquid includes sufficient quantities of nutrients and water to allow the algae to thrive and multiply until the filter is first used and then to maintain the algae colony once in use. The liquid may be taken from the algae growth colony as previously described.

In use, gaseous carbon dioxide 135 enters entry membrane 125 through connecting pipe 115 and exhaust pipe 100. As gaseous carbon dioxide 135 passes through liquid 140, some passes into solution in liquid 140. Algae 145 uses both gaseous carbon dioxide 135 and carbon in solution with liquid 140 along with light entering the filter through transparent body 152 to perform photosynthesis, converting carbon dioxide into oxygen and sugars. The sugars provide algae 145 with energy to grow, thus increasing the amount of algae 145 and the efficiency of filter 150.

When the engine is not running and gaseous carbon dioxide is not present in ample amounts, the colony of algae survives by the carbon dioxide which enters entry membrane 125 from exhaust port 153.

When light is not present exterior to filter 150, the algae in the device enters a light independent reaction using oxygen and sugar to produce water and carbon dioxide.

In an alternate preferred embodiment, also shown in FIG. 1 photo strips 154 are included on the interior surface of transparent body 152. Photo strips 154 include a translucent coating of a phosphorus paint encapsulated by transparent plastic layer 156. The phosphorus contained in photo strips 154 stores light energy and during the period when the device is exposed to light and then releases it during periods when the device is in the dark. The light released maintains the photosynthesis reaction and forestalls production of carbon dioxide by the device.

As oxygen is produced by algae 145, it is mixed with gaseous carbon dioxide, to become exit gases 155. Exit gasses 155 pass through exit membrane 130 and into the atmosphere. The design is such that gaseous carbon dioxide 135 flows through the device while interacting with algae within filter 150. Thus allowing the gaseous carbon dioxide 135 to become saturated in liquid 140 and providing algae 145 with carbon dioxide to convert into oxygen, thereby reducing overall pollutants.

Figure 2:
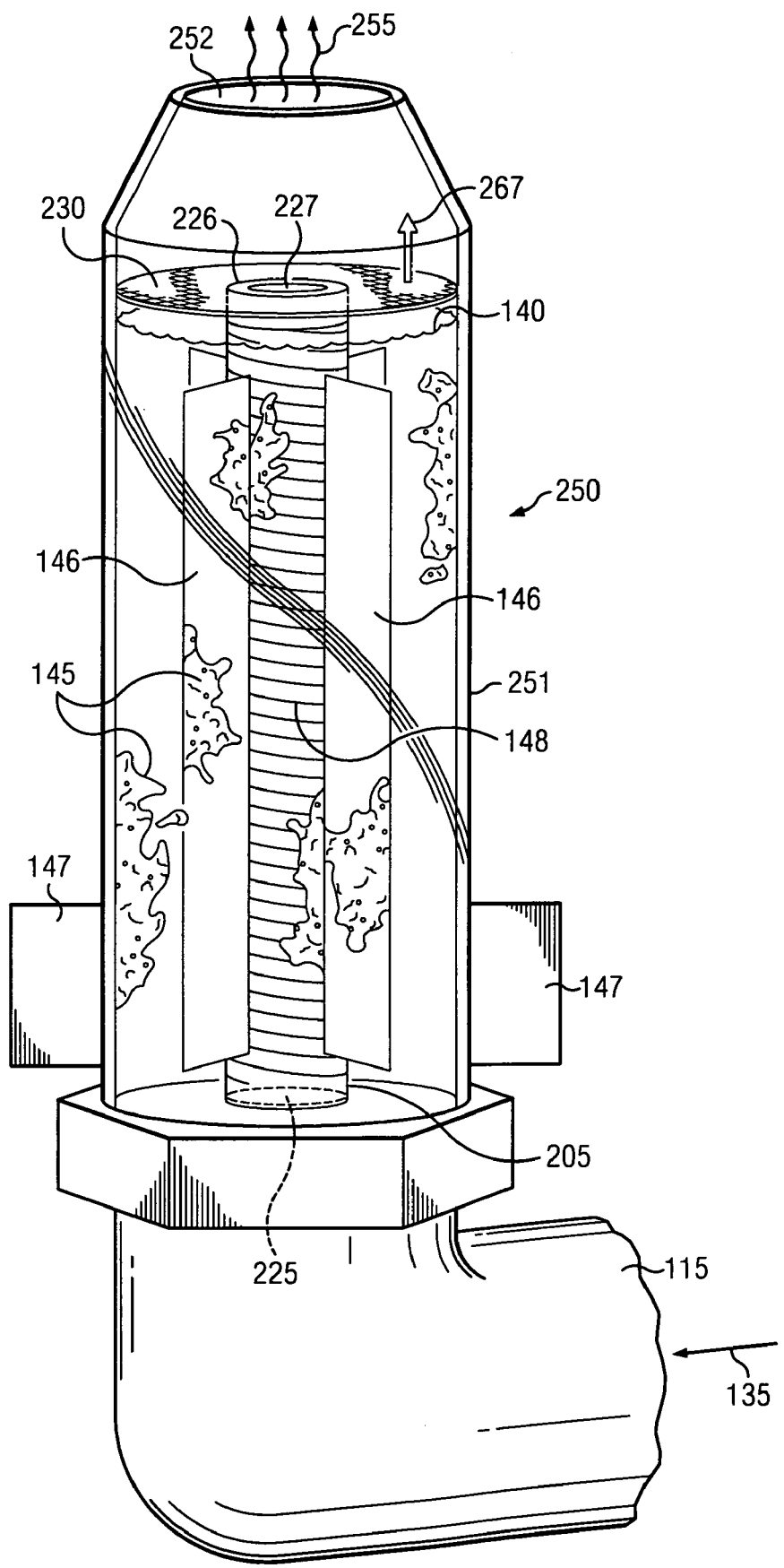
FIG. 2 shows an alternate embodiment consisting of a gas permeable tube surrounded by algae.

FIG. 2 shows an alternate embodiment of filter 250. Filter 250 includes transparent canister 251. Canister 251 contains liquid 140 and is bounded at one end by exit membrane 230 and at the other by entry membrane 225. This embodiment includes a central tube 205 which is gas permeable. Algae 145 grows on both central tube 205 and the inner walls of filter 250 and fins 146. Central tube 205 contains entry membrane 225 and is closed at cap 226. Integrally attached to central tube 205 are fins 146. Fins 146 provide heat transfer from the tube into liquid 140. Radial fins 147 are also attached to the exterior of canister 251, to shunt heat away from the canister.

In the preferred embodiment, central tube 205 is approximately 8 inches long and formed with wound polymer fibers 148, which allow for the concentration of the gaseous carbon dioxide. The tube is placed in a colony tank of algae, allowing the tube to be surrounded with the algae. The polymer fibers allow carbon dioxide to pass through the center of the tube and the algae, saturating liquid 140. The carbon dioxide passes through the device. As the algae perform photosynthesis, the carbon dioxide in the water solution is transformed into oxygen.

Gaseous carbon dioxide 135 enters entry membrane 225 and central tube 205. Since gas permeable, exhaust and gaseous carbon dioxide 135 passes through the body of the central tube 205 and enters liquid 140. The gaseous carbon dioxide reacts with algae 145. The increase in surface area of algae 145 to which liquid 140 is exposed causes an increase in efficiency in converting the carbon dioxide to oxygen. Oxygen produced by algae 145 and gaseous carbon dioxide 135 that does not enter solution with liquid 140 leaves as exit gases 255 through exit membrane 230.

Cap 226 includes control orifice 227. In one preferred embodiment the control orifice is used to throttle the exhaust and gaseous carbon dioxide 135 entering through entry membrane 225. In instances where engine pressures require a higher gaseous carbon dioxide flow rate than can be sustainably exited through central tube 205, the excess gaseous carbon dioxide exits through control orifice 227 and exit port 252.

Figure 3:
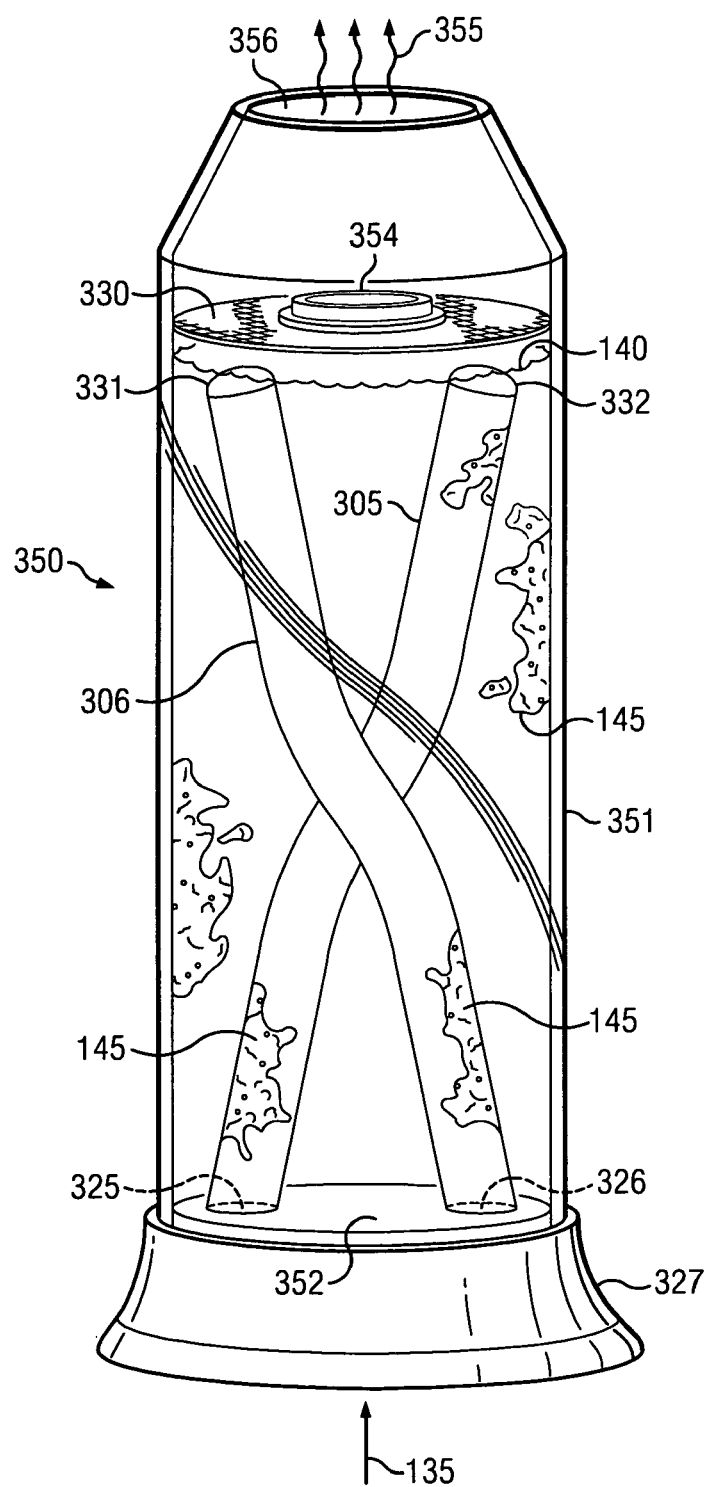
FIG. 3 shows an alternate embodiment with dual gas permeable tubes.

FIG. 3 shows an alternate embodiment of the invention composed of multiple tubes to enable a greater conversion of carbon dioxide by exposing the carbon dioxide saturated iron and water solution to a greater surface area of algae.

Filter 350 is comprised of canister 351 is a transparent cylinder. Canister 351 includes baffle 352 and entry membranes 325 and 326. Entry membranes 325 and 326 are dulcetly connected to flexible connector 327 which is in turn connected to the exhaust ports of an internal combustion engine (not shown). Baffle 352 directs gaseous carbon dioxide 135 and exhaust gases into entry membranes 325 and 326. Rigidly secured to entry membranes 325 and 326 are tubes 305 and 306, respectively. The tubes are gas permeable as previously described. The tubes are bounded by closed ends 331 and 332 respectively. Exit membrane 330 bounds upper end of canister 351.

Tubes 305 and 306 are encased with algae 145 concentrations on their exterior surfaces.

In use, gaseous carbon dioxide 135 passes through entry membranes 325 and 326 and into tubes 305 and 306. Gaseous carbon dioxide 135 passes through the semi-permeable walls and through algae 145 on the exteriors of tubes 305 and 306 and then into solution in liquid 140. This allows a greater surface area of algae 145 to be exposed to the gaseous carbon dioxide 135. Also, a corresponding higher rate of oxygen production due to photosynthesis by the algae within the filter occurs. The oxygen and remaining gaseous carbon dioxide leave the device as exit gases 355 through flow control nozzle 354 and exit orifice 356.

Flow control nozzle 354 serves to throttle exit gases 355 upon leaving liquid 140. The flow control nozzle is used to adjust the rate of the reaction and/or the rate of gas flow through the device.

Figure 4:
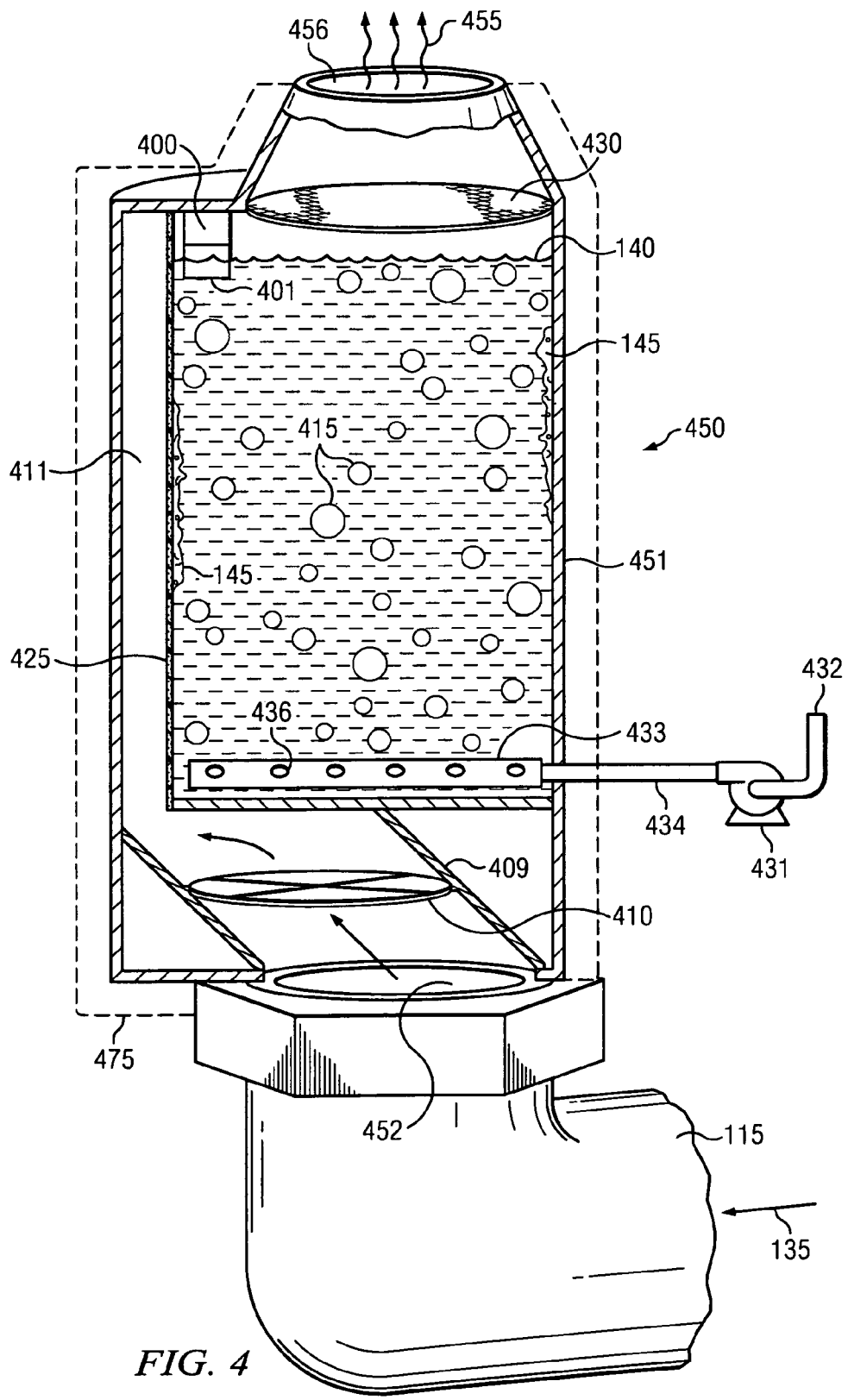
FIG. 4 shows an alternate embodiment that includes a bubbler.

FIG. 4 shows another alternate embodiment. This embodiment employs an air injection system to compress and inject ambient air into the canister to increase survivability of the algae and increase the rates and efficiency of photosynthesis.

In a preferred embodiment, the filter 450 includes canister 451. Canister 451 in the preferred embodiment is a stainless steel cylinder. Canister 451 includes entry orifice 452 which is connected to connecting pipe 115. Entry orifice 452 is also connected to duct 409 which communicate through check valve 410 to dispersion chamber 411. Check valve 410 resides in duct 409 between connecting pipe 115 and dispersion chamber 411. Check valve 410 prevents backflow of gaseous carbon dioxide 135 and exhaust gases.

Rigidly mounted within canister 451 is entry membrane 425. Entry membrane 425 is a gas permeable cylinder in ducted communication with dispersion chamber 411. Entry membrane 425 allows exhaust gases and gaseous carbon dioxide to penetrate the membrane while preventing liquid 140 from escaping. Entry membrane 425 contains liquid 140 including algae 145 as previously described. Algae 145 is dispersed in liquid 140 and also resident on the interior of entry membrane 425. Entry membrane 425 is bounded by exit membrane 430 which provides for exit of exit gases 455 through exit port 456.

Air pump 431 is a high pressure injection pump connected to a source of fresh air through air intake 432. Air pump 431 may be mechanically powered or electrically powered. Air pump 431 is connected to manifold 433 via conduit 434. Manifold 433 is included within entry membrane 425 and includes injection orifices 436. In operation, air pump 431 draws fresh air through air intake 432 forces it through conduit 434 through injection orifices 436 and into solution in liquid 140.

Further, circulation provided by the injected air allows spent algae cells to be moved away from the membrane thereby increasing exposure of live cells to exhaust gasses and the nutrient rich liquid.

Insulation 475 encapsulates canister 451. The preferred insulation is light weight and non-flammable; such as fiberglass or wool. However, other insulation may be used. Light 400 is located inside filter 450 to provide light for algae 145 to perform photosynthesis. This light may be tuned to the specific wavelengths most suited to the algae colony contained. Heat source 401 is provided inside entry membrane 425 to provide sufficient energy to prevent freezing of algae in inclement weather or when other freezing conditions occur. Power for both the light source and the heat source may be provided externally as known in the art.

In use, the gaseous carbon dioxide 135 and exhaust gas enters the device through connecting pipe 115. The gaseous carbon dioxide passes through check valve 410 which prevents reentry or backflow into connecting pipe 115. Gaseous carbon dioxide 135 passes through entry membrane 425. Gaseous carbon dioxide 135 passes through algae 145 in the form of exhaust bubbles 415 and into solution in liquid 140. As the carbon dioxide in the solution contacts surrounding algae 145, photosynthesis is carried out by the algae. Carbon monoxide, high temperature nitrogen and other toxic gases reduce the algae population. The mechanical mixing activity carried out by the injected air for manifold 433 moves dead cells are moved away from live cells thereby exposing more live cells to gaseous carbon dioxide 135.

Furthermore, air pump 431 can be active during periods when the internal combustion engine is not running, as can light 400 and heat source 401. Injected ambient air, including carbon dioxide, oxygen and other nutrients allows the algae colony to grow during periods of non use and thereby "heal" from the damage caused during digestion of carbon dioxide and carbon monoxide while the internal combustion engine is running. Exit gasses 455 pass through exit membrane 430 and exit port 456.

Figure 5:
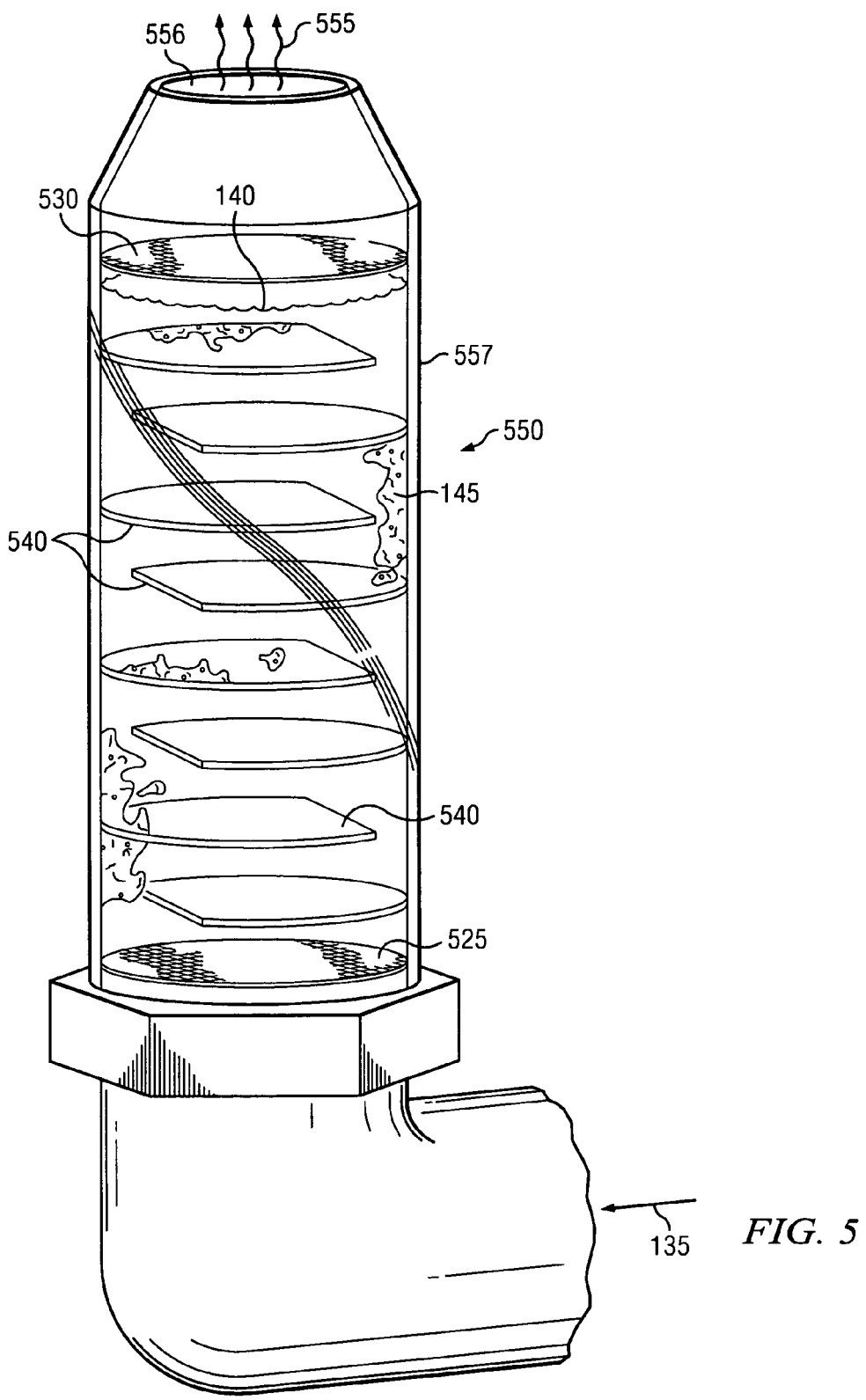
FIG. 5 shows an alternate embodiment that includes a baffle.

FIG. 5 shows another alternate embodiment. Filter 550 includes transparent cartridge 557. Transparent cartridge 557 is bounded by entry membrane 525 and exit membrane 530. Exit membrane 530 is dulcetly connected to exit port 556. Entry membrane 525 and exit membrane 530 are gas permeable but not liquid permeable. Transparent cartridge 557 provides a container for liquid 140. Gaseous carbon dioxide 135 enters filter 550 through entry membrane 525 pass around and through baffles 540 and exit though exit membranes 530 as exit gases 555. Baffles 540 are gas permeable such that gaseous carbon dioxide 135 passes through baffles 540 as a maze. Baffles 540 provide an increase in surface area of algae 145 in contact with gaseous carbon dioxide 135 and the carbon in solution with liquid 140. Each of these baffles 540 are encased with algae 145 which increases the efficiency of the photosynthesis reaction.

Figure 6:
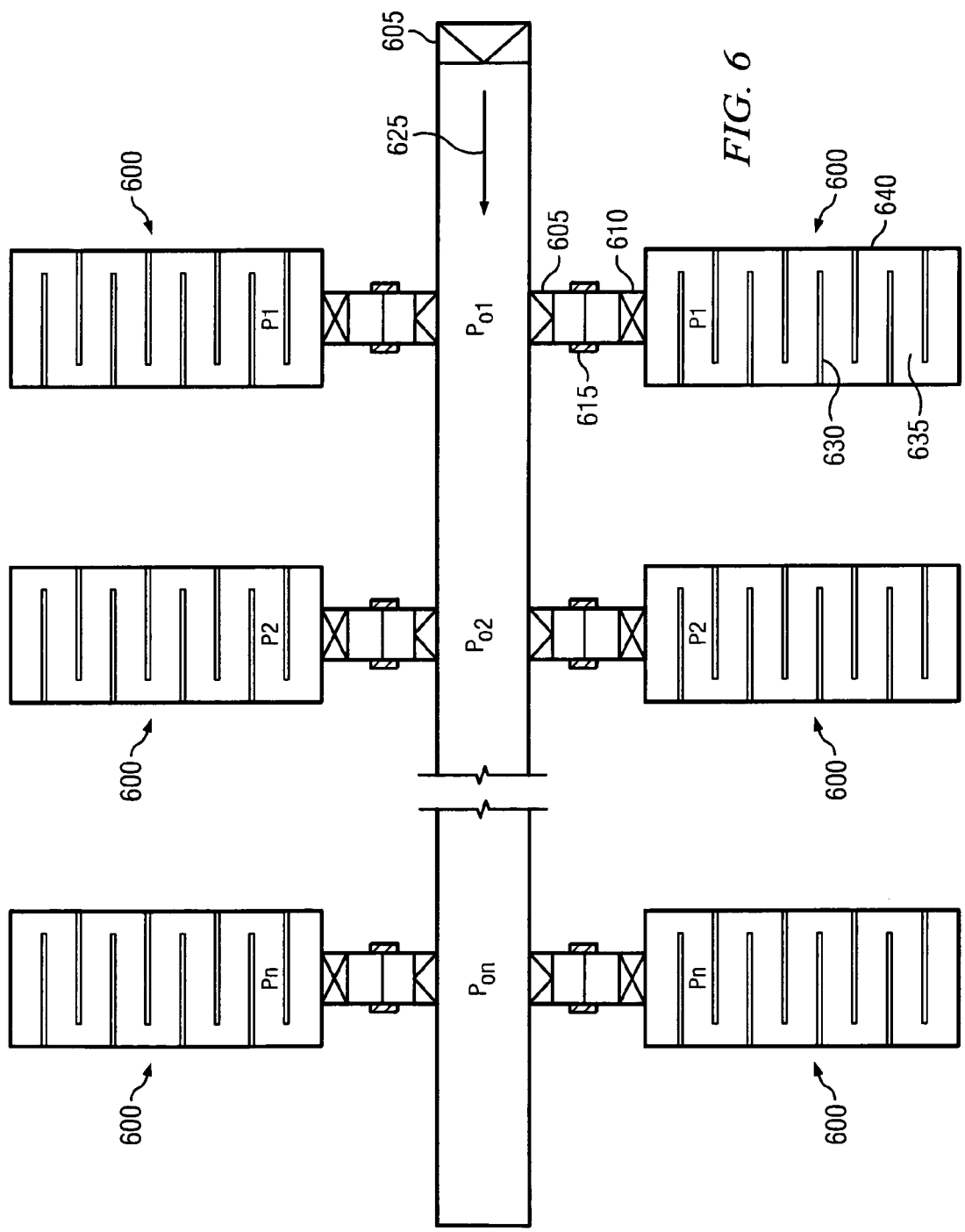
FIG. 6 shows an alternate embodiment applicable for larger and more permanent carbon producing sites.

FIG. 6 shows another alternate embodiment. In this embodiment, algae filters 600 are fixed and located adjacent a production source of gaseous carbon dioxide. For example, the source may be an electricity generation plant where natural gas or coal is burned to create energy. The filters contain the exhaust gas in a "used" environment until removed.

Each algae filter 600 includes a transparent vessel 640 to allow the passage of light. Each filter includes a nutrient solution 644 and charge of algae 645. Nutrient solution 644 is an iron sulfide and water solution in a preferred embodiment. However, other solutions that promote the growth and development of algae may be used. Each transparent vessel 640 includes a baffle 630. Each baffle 630 is coated with more alive deposit 631.

The filters are removably attached to main pipe 620 by means of removable coupling 615 attached to connecting pipe 602. Connecting pipe 602 includes a cutoff valve 610 and pressure valve 605. Cutoff valve 610 opens and closes the flow of gaseous carbon dioxide to filter 600, each cutoff valve can be set to a different pressure. When the cutoff pressure is reached the cutoff valve automatically closes. Filter 600 to be removed by means of removable coupling 615. Pressure valve 605 allows the pressure within the filter 600 to equalize with the pressure within main pipe 620.

In use, gaseous carbon dioxide 625 flows into past main shut off valve 604 into main pipe 620. Gaseous carbon dioxide 625 enters each filter 600 through pressure valve 605 and connecting pipe 602, past cutoff valve 610 and removable coupling 615.

At pressure $Po_1$, pressure valve 605 allows a balance of pressure between the main pipe 620 and the vessels exposed to pressure P1. As flow proceeds, pressure drops in main pipe 620 to $Po_2$ causing the cutoff valves 610 associated with P1 to close and the cutoff valves 610 associated with $Po_2$ to open. The pressure of filters 600 associated with pressure P2 are then filled with gaseous carbon dioxide 625 from main pipe 620 as described above. When pressure of $Po_2$ is reached, main shut off valve 604 closes the filter system. A similar process occurs at $P_{on}$ associated with $P_n$. The size of filters 600 may be determined by the pressure and rate at which gaseous carbon is released.

A benefit of this system is that the gaseous carbon dioxide remains locked in the system until it is converted to oxygen by the algae within filter 600. The increased pressure within the filter increases the amount of gaseous carbon dioxide 625 entering nutrient solution 644. Additionally, the system is modular, such that any filter 600 that becomes delivered may be replaced by another.

The invention claimed is:

1. A carbon dioxide filter apparatus comprising:
    a transparent canister having an entry port and an exit port, an interior surface and an external surface;
    the entry port comprising a first gas permeable membrane;
    the exit port comprising a second gas permeable membrane;
    the canister including a first deposit of algae on the interior surface and containing a nutrient liquid; and
    whereby when carbon dioxide enters the first gas permeable membrane and contacts the deposit of algae, the deposit of algae provides a photosynthesis reaction producing oxygen, which exits through the second gas permeable membrane;
    a central tube operatively disposed in the canister, bounding the entry membrane, and providing an exit port;
    the central tube being comprised of a third gas permissible membrane and incorporating a pattern of polymer fibers;
    the central tube including a second deposit of algae adjacent the pattern of polymer fibers;
    whereby carbon dioxide enters the entry port and traverses the third gas permissible membrane and reacts with the first deposit of algae and the second deposit of algae to form oxygen; and
    whereby the oxygen escapes through the exit port.

2. The filter apparatus of claim 1 wherein the entry port is removably connected to a source of gaseous carbon dioxide.

3. The apparatus of claim 1 further comprising a light source, adjacent the algae, the light source being drawn from the group of electrical and chemical.

4. The apparatus of claim 1 further comprising a heat sink operatively connected to the central tube.

5. The apparatus of claim 1 wherein the central tube is comprised of a titanium alloy.

6. The apparatus of claim 1 further comprising a heat sink operatively connected to the transparent canister.

7. A carbon dioxide filter apparatus comprising:
    a transparent canister having a first entry port, a second entry port, and an exit port;
    the first entry port comprising a first gas permeable membrane;

the second entry port comprising a second gas permeable membrane;
the exit port comprising a third gas permeable membrane;
a first sealed digestion tube, comprised of a fourth gas permeable membrane, connected to the first gas permeable membrane and resident diagonally in the canister;
a second sealed digestion tube, comprised of a fifth gas permeable membrane, connected to the second gas permeable membrane and resident diagonally in the canister;
the first sealed digestion tube supporting a first colony of algae;
the second sealed digestion tube supporting a second colony of algae;
the canister containing a liquid nutrient adjacent the first sealed digestion tube and the second sealed digestion tube; and
whereby gaseous carbon dioxide enters the first entry port and the second entry port and the first colony of algae and the second colony of algae, in the presence of light through the canister, provide a photosynthesis reaction eliminating at least a fraction of the gaseous carbon dioxide and producing oxygen that exits through the exit port as an escaping gas.

8. The apparatus of claim 7 further comprising a flow control nozzle adjacent the exit membrane to control a flowrate of the escaping gas.

9. A filter for gaseous carbon dioxide apparatus comprising:
a support canister having an entry port and an exit port;
the exit port including an exit membrane;
the entry port connected to a dispersion chamber;
the disposition chamber ductedly connected to an entry membrane; the entry membrane being gas permeable;
a manifold operatively contained within the entry membrane;
the manifold connected to a source of ambient air pressure;
a nutrient liquid contained by support membrane;
a colony of vilified algae resident within the nutrient liquid;
a light source adjacent the colony of vilified algae; and
whereby when the light source is active and gaseous carbon dioxide under pressure enters the entry membrane, ambient air escapes into the nutrient liquid from the manifold and the colony of vilified algae provides a photosynthesis reaction to reduce a portion of the gaseous carbon dioxide to gaseous oxygen; the gaseous oxygen exiting through the exit membrane.

10. The apparatus of claim 9 further comprising an insulated material at least partially surrounding the support canister.

11. The apparatus of claim 9 further comprising a heat source adjacent the colony of vilified algae.

* * * * *